United States Patent [19]
Dunphy et al.

[11] 3,958,558
[45] May 25, 1976

[54] IMPLANTABLE PRESSURE TRANSDUCER

[75] Inventors: Roderick R. Dunphy, San Jose; Leo A. Bullara, Glendora; Robert H. Pudenz, Pasadena, all of Calif.

[73] Assignee: Huntington Institute of Applied Medical Research, Pasadena, Calif.

[22] Filed: Sept. 16, 1974

[21] Appl. No.: 506,217

[52] U.S. Cl. ............................ 128/2 P; 128/2.05 E; 128/2.1 A; 73/398 R; 73/398 C; 73/410
[51] Int. Cl.² ............................................ A61B 5/02
[58] Field of Search ............ 128/2.1 A, 2 P, 2.05 D, 128/2.05 E; 73/398 R, 398 C, 399, 410

[56] References Cited
UNITED STATES PATENTS

| | | | |
|---|---|---|---|
| 2,958,781 | 11/1960 | Marchal et al. | 128 2 P X/ |
| 3,034,356 | 5/1962 | Bieganski et al. | 73/398 R |
| 3,144,017 | 8/1964 | Muth | 128/2 P |
| 3,583,387 | 6/1971 | Garner | 128/1 R |
| 3,638,496 | 2/1972 | King | 73/398 R |
| 3,738,356 | 6/1973 | Workman | 73/398 R X |

OTHER PUBLICATIONS
*Electronics*, Mar. 22, 1963, pp. 58–60.

*Primary Examiner*—Kyle L. Howell
*Attorney, Agent, or Firm*—Christie, Parker & Hale

[57] ABSTRACT

A wireless, surgically implantable pressure transducer for measuring pressure of fluid or tissue in a body chamber such as brain ventricle of a patient suffering hydrocephalus or a severe head injury. The transducer includes a coaxial variable capacitor electrically connected across an inductor to form a parallel resonant L-C circuit. Alternatively, a coaxially variable inductor may be connected across a capacitor to form the L-C circuit. A bellows is mechanically connected to the variable component to vary the value of capacitance or inductance and hence the resonant frequency of the L-C circuit in response to pressure changes of the fluid in which the bellows is immersed. The transducer is electromagnetically coupled to an external source of variable-frequency oscillatory energy such as a grid-dip oscillator which enables external detection of the transducer resonant frequency which is in turn indicative of the level of fluid pressure being sensed.

7 Claims, 5 Drawing Figures

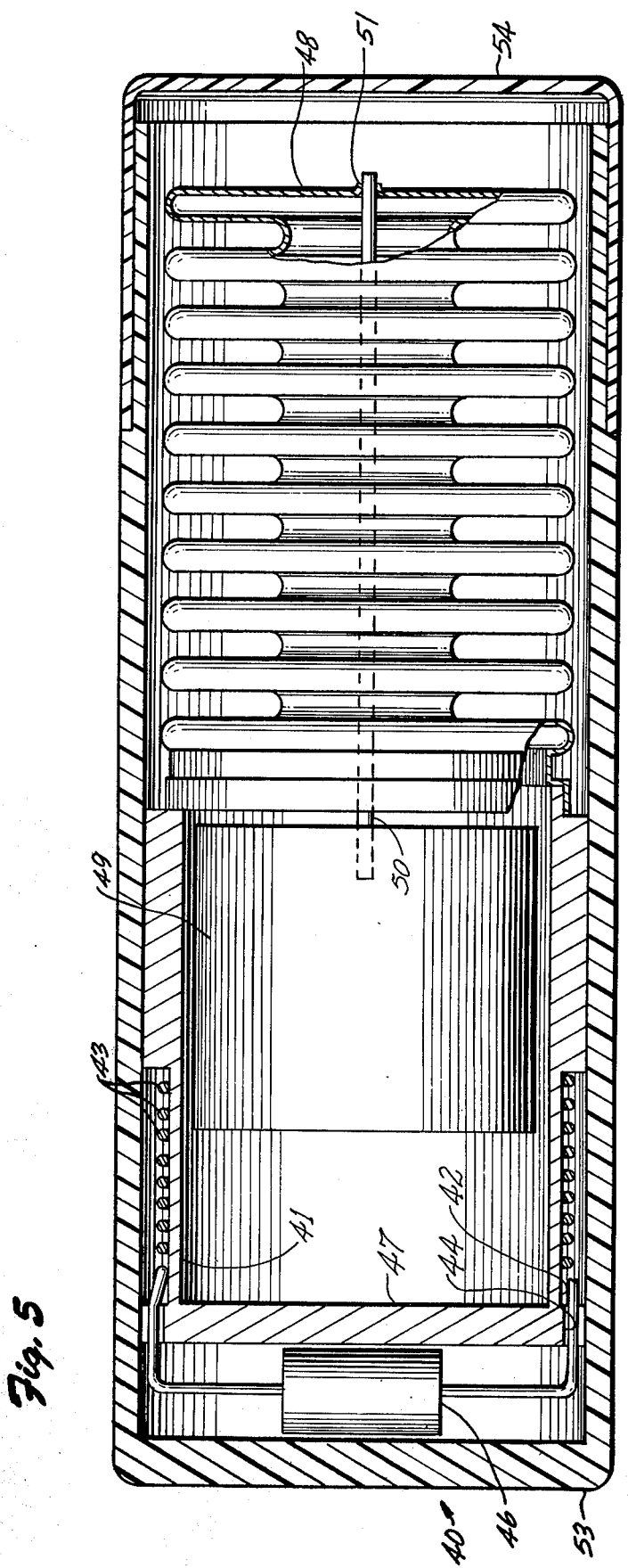

IMPLANTABLE PRESSURE TRANSDUCER

BACKGROUND OF THE INVENTION

Hydrocephalus is a brain condition in which cerebrospinal fluid accumulates at abnormally high pressure in ventricles or chambers within the brain. The ventricles expand in response to the pressure exerted by the fluid, and surrounding brain tissue is compressed between the ventricles and the skull. Hydrocephalus usually occurs in babies or young children, and, if unchecked, results in brain damage, enlargement and deformation of the head, and eventual death.

Modern medical methods are effective in arresting many cases of hydrocephalus, but it is often desirable to monitor pressure of the cerebrospinal fluid over an extended period to detect relapse and to determine long-range effectiveness of treatment. In the past, this measurement has been made by surgically implanting a miniature but generally conventional transducer such as a strain-gage-bridge pressure pickup. This technique requires that wiring be conducted from the implanted transducer to external instrumentation which provides excitation voltage to the bridge and detects bridge-unbalance voltage signals indicative of pressure. Alternatively, non-electrical manometric measurement methods may be used, but these techniques require installation of a conduit extending from the interior of the brain ventricle through the skull and scalp to external measurement equipment.

The primary disadvantage of these known techniques is that they involve conducting an electrical cable or fluid tube through the skull and scalp to enable direct electrical or mechanical connection between the interior of the brain ventricle and external equipment. This connection is disturbing and uncomfortable for the patient, and the danger of infection of tissue surrounding the cable or tube (and the risk of infection spread resulting in meningitis, ventriculitis, brain abscess or septicemia) requires constant supervision and usually full-time hospitalization of the patient. There is accordingly a need for a measuring device which does not require direct electrical or mechanical connection from the brain to external equipment, and which permits the patient to be ambulatory after the device is installed.

Connection-free implantable transducers have been previously proposed, and they typically function by external detection of the resonant frequency of a resonant circuit in the implanted device. For example, the prior art includes a biological pressure transducer for sensing pressure in the gastrointestinal tract and having a resonant circuit with a pressure-controlled inductor. Wireless systems are also used for sensing EEG or ECG voltages, the implantable part of the system using an electrically variable capacitor in a resonant circuit. A wireless resonantcircuit transducer has also been used for measuring intraocular pressure, the transducer using a pair of variably spaced Archimedean-spiral coils mounted on pressure-sensitive diaphragms.

The transducer of this invention operates in wireless fashion similar to the instruments described above, but provides improved performance and lower drift in implantation applications involving placement in body cavities such as brain ventricles or heart chambers where only a very small transducer can be tolerated. The transducer and is disclosed below in a specific form suitable for intracranial implantation to monitor pressure of cerebrospinal fluid in a brain ventricle. This form is also suitable for mounting on hydrocephalus shunt apparatus as often used in treating and controlling this disease.

Our transducer is, however, also suitable for implantation elsewhere in the body, and is believed to be useful in any application where a very small, implantable and wireless device is needed to measure fluid or tissue pressure. For example, the transducer is believed useful for either short- or long-term monitoring of abnormal intracranial pressure in head-injury patients, or for post-surgical monitoring of brain-tumor victims to detect possible recurrence of the tumor. When such monitoring is no longer needed, the implanted transducer is removed by a simple re-opening and closure of the overlying scalp tissue.

SUMMARY OF THE INVENTION

Briefly stated, the transducer of this invention is a sealed housing having an outer surface formed of a biologically compatible material, the housing having a pressure-sensing means such as a bellows extending therefrom. Preferably, the bellows is isolated from direct contact with the biological fluid to be monitored by a flexible balloon-like enclosure which extends from the housing around the bellows, a space between the enclosure and bellows being filled with a buffer fluid such as distilled water.

An inductor assembly is mounted within the housing, and in one form is a hollow ferrite core having a conductive coil wound on its outer surface. A variable capacitor assembly, preferably a coaxial piston-cylinder type, is fitted within the core and includes a movable element connected to the pressure-sensing means to vary capacitance of the capacitor in response to changes in pressure of the fluid being monitored and in which the transducer is immersed. The capacitor is electrically connected across the inductor to form a resonant L-C circuit, the resonant frequency of which is varied by changes in the fluid pressure applied to the bellows or similar means which in turn drives the capacitor movable element. In another form of the invention, a coaxially variable inductor is mechanically coupled to the pressure-sensing means and electrically connected across a capacitor to form a pressure-controlled, variable-resonant-frequency L-C circuit. The transducer is implanted in the body to measure pressure of surrounding fluid or tissue. In one important application, the transducer is positioned within a brain ventricle to sense pressure of cerebrospinal fluid or surrounding tissue in this body chamber. There is no direct electrical connection from the transducer to equipment external to the chamber. The resonant frequency of the L-C circuit is monitored by wireless transmission of electromagnetic energy from an external generator such as a grid-dip oscillator, thereby providing resonant-frequency data which is analogous to fluid or tissue pressure in the chamber.

BRIEF DESCRIPTION OF THE DRAWINGS

FIG. 5 is a side sectional elevation of an alternative and presently preferred transducer according to the invention and using a variable inductor.

DESCRIPTION OF THE PREFERRED EMBODIMENT

Figure 1:
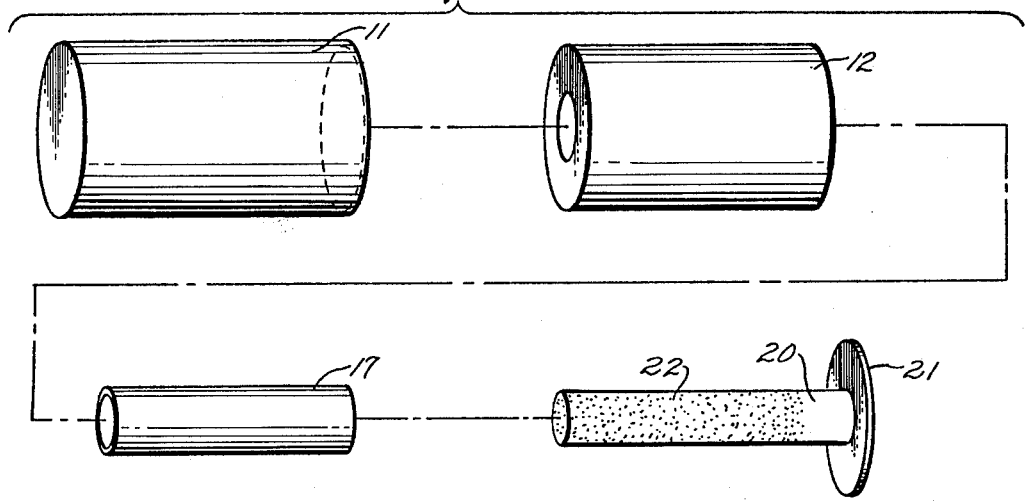
FIG. 1 is an exploded view of a portion of a pressure transducer according to the invention.
Figure 2:
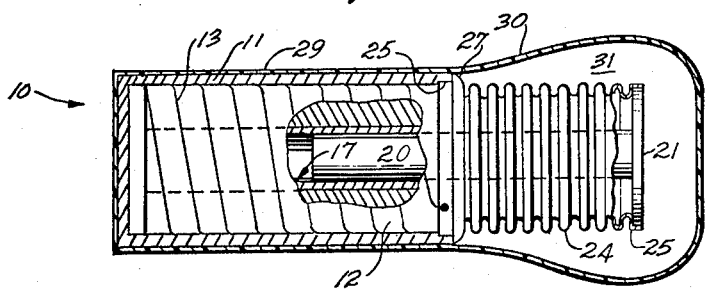
FIG. 2 is a side elevation, partly in section, of the assembled transducer.
Figure 3:
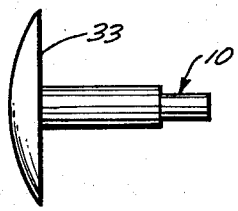
FIG. 3 is a side elevation of the transducer mounted on a plug for intracranial installation.

Referring to FIGS. 1–2, a pressure transducer 10 according to the invention includes a housing 11 which is preferably a hollow cylindrical cup of cast plastic as sold under the trademark "Hysol." In a typical form, the housing is 0.550-inch long, and has outside and inside diameters of 0.275 and 0.260-inch respectively.

A hollow cylindrical ferromagnetic core 12 is sized to make a loose fit within housing 11, and the core is typically 0.500-inch long, with outside and inside diameters of 0.250 and 0.125-inch respectively. The core is preferably made from a sintered ferrite material such as sold by Indiana General Division of Electronic Memories Magnetics Corporation as "Q-2 Ferramic" material.

Figure 4:
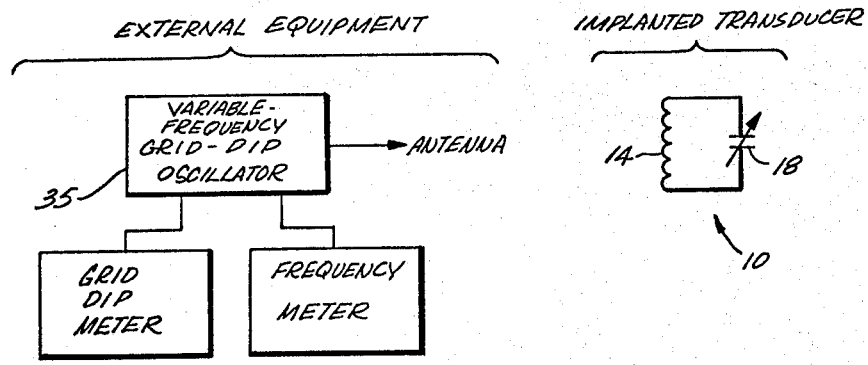
FIG. 4 is a block diagram of external electronic equipment used with the transducer.

A coil 13 (FIG. 2) is formed by helically wrapping about 10 turns of a conductor such as 0.020-inch-diameter gold wire around the outside surface of core 12. Core 12 and coil 13 form an inductor 14 for the transducer as shown in the electrical schematic in FIG. 4.

A hollow cylindrical sleeve 17 (FIGS. 1–2) of a non-ferrous material such as brass forms a fixed electrode of a coaxial variable capacitor 18 (FIG. 4) in transducer 10. The sleeve is sized to make a snug slip fit within core 12, and is typically 0.400-inch long with outside and inside diameters of 0.124 and 0.100-inch respectively.

A rod or piston 20, having a thin, integrally formed and radially extending flange 21 at one end, is also made from a non-ferrous material such as brass. A portion of the outside of the rod is covered with a thin dielectric coating 22 of a material such as tantalum pentoxide. The piston fits into sleeve 17 in piston-cylinder fashion, and forms a movable element or electrode of coaxial variable capacitor 18. The piston has an overall length of about 0.500-inch, and the piston and flange have diameters of about 0.095 and 0.020-inch respectively.

A generally cylindrical bellows 24 (FIG. 2) provides a force-summing surface for transducer 10, the bellows varying in length according to the pressure of fluid in which the transducer is immersed. A typical and suitable bellows is sold by Servometer Corporation as a Type SK4681. The bellows is made of an electrically conductive material which is preferably gold-plated nickel. The ends of the bellows are open, and each end defines an axially extending shell or flange 25.

To assemble the transducer, capacitor sleeve 17 is cemented within core 12, the left ends (as viewed in FIG. 2) of these components being flush. The left end of coil 13 is drawn around the end of core 12 and soldered into electrical contact with the sleeve. Flange 25 at the left end of bellows 24 is then slipped over the right end of core 12 and cemented in place. The right end of coil 13 is soldered or otherwise bonded into electrical contact with the bellows flange as shown in FIG. 2.

Capacitor piston 20 is then fitted through the bellows into sleeve 17, and flange 21 of the piston is secured within flange 25 at the right end of the bellows, the attachment being made with an electrically conductive cement such as a conductive silver-epoxy or gold-epoxy adhesive. The capacitor piston is thus electrically connected to the right end of coil 13 through bellows 24. Sealing of the transducer is completed by placing an annular body 27 of epoxy resin or a similar sealant between the right end of housing 11 and the bellows.

The transducer interior is hermetically sealed from the outside environment so fluid cannot seep into the bellows or variable coaxial capacitor. Preferably, the transducer is evacuated prior to final sealing, and is back-filled with dry nitrogen. Back-filling is normally done at one atmosphere of pressure to provide a transducer which functions as a "sealed gage pressure" measuring device, but other pressures may be used if a reference pressure other than one atmosphere is preferred.

Preferably, housing 11 is sheathed in a covering 29 of a biologically compatible material such as plastic sold under the trademark "Silastic." In a preferred embodiment, covering 29 is extended to form a loose balloon-like enclosure 30 around bellows 24, and enclosure 30 is filled with distilled water 31, or preferably with a fluid which approximates the composition of the fluid being monitored (such as Elliot's 'B' solution when cerebrospinal fluid is being monitored) to provide a correct ionic balance on both sides of the enclosure. Pressure of the fluid being monitored is transmitted through enclosure 30 and water 31 to actuate bellows 24, but the enclosure and water form a chemical and mechanical buffer preventing tissue encroachment which could interfere with free compression and extension of the bellows.

When used as an intracranial implant in a brain ventricle or in brain tissue, transducer 10 is preferably mounted on a flanged plug 33 of a material such as Silastic plastic. Surgical installation of this equipment involves generally the same procedures used in installing hydrocephalus shunts or pressure absorbers, these procedures being briefly discussed in U.S. Pat. No. 3,583,387—Garner and Bullara titled "Pressure Absorbing Appliance for Treating Hydrocephalus."

The values of inductance and capacitance of the parallelconnected inductor and capacitor of transducer 10 can be computed and pre-determined using known engineering formulae. Circuits having nominal resonant frequencies in the range of about 30 to perhaps 100 megaHertz are believed best suited for biological applications. Higher frequencies (e.g., 200 mHz) have some advantages, but low "Q's" typically experienced in tissue at these frequencies tend to obscure the accurate external detection of resonance of the transducer L-C circuit.

Pressure range of the transducer is determined primarily by the mechanical performance of bellows 24, and these displacement-versus-pressure characteristics can also be calculated by known engineering formulae. Typical units we have tested have had an operating pressure range of 0 to 1000 millimeters of water (gage), and the transducer L-C circuit has been designed to have a zero-pressure resonant frequency of about 82 mHz. As the fluid pressure is increased, bellows 24 contracts to drive capacitor piston 20 into sleeve 17, thereby increasing the capacity of the coaxial capacitor and decreasing the resonant frequency of the circuit. A change in resonant frequency of about 20 mHz is typically obtained in driving the transducer from zero to full-scale pressure.

In use, the installed transducer is irradiated with electromagnetic energy transmitted through the body and generated by an external variable-frequency oscillator. Some of this radio-frequency energy is absorbed (and also reflected or retransmitted) by the resonant circuit, depending on how close the incident frequency is to the resonance frequency of the circuit. The frequency of the external oscillator is varied or swept until resonance of the transducer L-C circuit is externally detected. This resonant frequency is in turn indicative of the internal fluid pressure being sensed by the transducer.

A simple and accurate way to detect internal transducer resonance with an external circuit involves use of a grid-dip oscillator 35 (FIG. 4) which shows a sharp drop or "valley" in grid current when the resonant point of the "receiving" circuit is swept through by the "transmitting" oscillator. The oscillator is preferably used in conjunction with a conventional electronic frequency counter which provides a direct visual readout of frequency at the resonant point.

External phase-sensitive equipment can also be used to detect the characteristic and marked phase shift which occurs when the resonant circuit receives energy at its resonant frequency. Other external detection systems are discussed in the aforementioned article from IEEE Transactions on Bio-Medical Engineering and the references therein cited.

Prior to installation, the transducer is calibrated by immersing it in a fluid (e.g., Elliot's 'B' solution) having characteristics similar to the biological fluid or tissue to be eventually monitored. The pressure of the test fluid is then varied under controlled conditions while the resonant frequency of the transducer is tracked as described above to develop a pressure-versus-frequency calibration curve.

The transducer of this invention can also be made with a variable-reactance element which is a coaxial variable inductor connected across a fixed capacitor, or both the capacitive and inductive components can be variable under control of the pressure-sensitive bellows. A presently preferred embodiment of the invention is shown as a transducer 40 in FIG. 5.

Transducer 40 includes a cup-shaped hollow cylindrical coil-supporting sleeve 41 which is preferably made of polytetrafluorethylene plastic or a medical-grade acrylic plastic. The sleeve has an annular recess 42 in which is wound an inductive coil 43 of say 12 turns of 0.005-inch-diameter copper or gold insulated wire. The ends of the coil are fed through a pair of longitudinal slots 44 at one end of sleeve 41 for connection to a miniature fixed capacitor 46 mounted on a wall 47 which closes one end of the sleeve. The coil and capacitor are preferably "potted" in a medical-grade paraffin (not shown).

A bellows 48 (generally corresponding to bellows 24 described above) is fitted over and secured to the open end of sleeve 41. A solid cylindrical ferrite core 49 is positioned within sleeve 41 to form an inductor with coil 43. A stiff metal shaft 50 (preferably a length of stainless-steel tubing of about 0.009-inch outside diameter as used in hypodermic needles) is secured to the core and extends therefrom through a central opening 51 in the closed end of bellows 48. During assembly of the transducer, the "zero" position of the core is adjusted to provide a desired inductance of the coil and core, and shaft 50 is then permanently secured to the bellows to support the core and seal opening 51.

A cup-shaped housing 53 made of medical-grade acrylic plastic is slipped over and secured to sleeve 41. An enclosure 54 is fitted over and sealed to the open end of housing 53, and this enclosure is preferably a membrane of Silastic plastic sheet. The space between the outer surface of the bellows and the inner surfaces of the membrane and housing is filled with distilled water or a fluid compatible with the characteristics of the fluid being monitored as described above.

The dimensions of housing 53 are about 0.165-inch diameter by 0.445-inch length, and a very compact assembly is provided which is suitable for implantation. A nominal resonant frequency of about 80 mHz is provided by using a capacitor of 5 picofarads and an inductance of about 0.8 microhenries. Installation and use of transducer 40 corresponds to the procedures discussed above with respect to transducer 10.

There has been described a compact variable-resonance-frequency pressure transducer using a coaxial variable capacitor or inductor controlled by pressure-sensing means such as a bellows. The use of coaxial variable-reactance components permits packaging of the transducer in a compact size and shape which enables wireless implantation in body chambers which heretofore were monitored effectively only with attached-wire measurement systems.

We claim:
1. An implantable pressure transducer, comprising:
   an elongated housing having an axis of elongation;
   a capacitor assembly mounted in the housing;
   an inductor assembly mounted in the housing and connected across the capacitor assembly to form a resonant L-C circuit;
   one of the assemblies being of coaxial form and including an axially movable element for varying the reactance thereof, the element being movable along the axis of elongation;
   a pressure-sensitive bellows secured and sealed to one end of the housing and effective to generate a displacement in response to applied pressure;
   means connecting the bellows and the axial movable element whereby bellows displacement resulting from applied pressure is transmitted by the connecting means to move the element and thereby vary the resonant frequency of the L-C circuit in response to applied pressure, said resonant frequency being externally detectable by wireless transmission of electromagnetic energy between external equipment and the implanted transducer to provide data analogous to pressure; and
   a flanged plug secured to an end of the housing opposite the end on which the bellows is mounted;
   the transducer being free of external wired connections and having outer surfaces formed of materials suitable for human implantation, the inductor and capacitor assemblies being isolated within the housing against contact with biological material in which the transducer is implantable.

2. The transducer defined in claim 1 wherein said one assembly is a piston-cylinder capacitor assembly including a hollow conductive sleeve forming a stationary element, and in which the axially movable element is a rod making a non-conductive slip fit in the sleeve.

3. The transducer defined in claim 2 wherein the inductor assembly comprises a ferromagnetic hollow core, and a conductive coil wound around the outer surface of the core, the coil being connected at opposite ends to the stationary and movable capacitor elements respectively, the stationary element being fitted within the core.

4. The transducer defined in claim 1 wherein the inductor assembly comprises a coil connected across the capacitor assembly, and a ferrous core positioned within the coil and forming said axially movable element.

5. The transducer defined in claim 1 wherein the housing includes a flexible covering extending around the bellows to form a sealed clearance space between the covering and bellows, and further including a body of liquid filling the clearance space.

6. The transducer defined in claim 5 wherein said connecting means comprises a hollow shaft secured at opposite ends to the axially movable element and a movable end of the bellows.

7. A system for measuring biological pressures, comprising:
   an elongated and biologically implantable housing having an axis of elongation;
   a capacitor assembly mounted in the housing;
   an inductor assembly mounted in the housing and connected across the capacitor to form a resonant L-C circuit;
   one of the assemblies being of coaxial form and including an axially movable element for varying the reactance thereof, the element being movable along the axis of elongation;
   pressure-sensing means mounted on the housing and effective to generate a displacement in response to applied pressure;
   means connecting the pressure-sensing means and the axially movable element whereby displacement of the pressure-sensing means is transmitted by the connecting means to move the element and thereby vary the resonant frequency of the L-C circuit in response to applied pressure;
   a flexible covering secured to the housing and extending over the pressure-sensing means to form a sealed clearance space between the covering and pressure-sensing means, and further including a body of liquid filling the clearance space whereby a biological fluid pressure to be sensed is exerted on the covering and transmitted through the covering and liquid to the pressure-sensing means;
   the implantable housing being free of external wired connections and having outer surfaces formed of materials suitable for human implantation, the inductor and capacitor assemblies being isolated within the housing against contact with biological material in which the transducer is implantable; and
   external means for wireless transmission of electromagnetic energy to the implantable L-C circuit, and for detecting the resonant frequency of the circuit.

* * * * *